US007812213B2

(12) United States Patent
Doverbo et al.

(10) Patent No.: US 7,812,213 B2
(45) Date of Patent: Oct. 12, 2010

(54) ABSORBENT ARTICLE WITH THROUGH-SLITS SURROUNDED BY BINDING AREAS

(75) Inventors: Anna-Gerd Doverbo, Mölndal (SE); Robert Kling, Skene (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 10/905,327

(22) Filed: Dec. 28, 2004

(65) Prior Publication Data
US 2005/0148983 A1 Jul. 7, 2005

Related U.S. Application Data

(60) Provisional application No. 60/532,575, filed on Dec. 29, 2003.

(51) Int. Cl.
*A61F 13/15* (2006.01)
*A61F 13/20* (2006.01)

(52) U.S. Cl. ............... 604/358; 604/378; 604/383; 604/385.01; 604/385.23

(58) Field of Classification Search ......... 604/385.101, 604/385.23, 385.01, 379–383, 358, 385.09, 604/385.12; 428/131–137
See application file for complete search history.

(56) References Cited

U.S. PATENT DOCUMENTS

| 3,468,311 | A | * | 9/1969 | Gallagher | 604/370 |
| 3,886,941 | A | * | 6/1975 | Duane et al. | 604/370 |
| 4,055,180 | A | * | 10/1977 | Karami | 604/368 |
| 4,336,803 | A | * | 6/1982 | Repke | 604/385.25 |
| 4,389,211 | A | * | 6/1983 | Lenaghan | 604/383 |
| 4,626,254 | A | | 12/1986 | Widlund et al. | |
| 4,634,440 | A | * | 1/1987 | Widlund et al. | 604/383 |
| 4,690,679 | A | * | 9/1987 | Mattingly et al. | 604/383 |
| 4,859,519 | A | * | 8/1989 | Cabe et al. | 428/131 |
| 4,895,568 | A | * | 1/1990 | Enloe | 604/385.27 |

(Continued)

FOREIGN PATENT DOCUMENTS

EP 0 304 957 A3 3/1989

(Continued)

OTHER PUBLICATIONS

Description of Office Action in corresponding Columbian patent application.

(Continued)

*Primary Examiner*—Leslie R Deak
*Assistant Examiner*—Adam Marcetich
(74) *Attorney, Agent, or Firm*—Buchanan Ingersoll & Rooney PC

(57) ABSTRACT

An absorbent article having a liquid-permeable cover sheet, a liquid-impermeable cover sheet, and an absorption body arranged between the cover sheets. The article defines a longitudinal direction, a front portion in the longitudinal direction, and a rear portion in the longitudinal direction. The upper cover sheet, together with an underlying wadding material, defines a laminate which, at least in the rear portion, is designed with at least one through-slit which defines an opening for passage of bodily excretions through the slit, and the slit is surrounded by binding areas which, together with a resilient action of the wadding material, define a raised area on the surface of the article.

29 Claims, 4 Drawing Sheets

U.S. PATENT DOCUMENTS

| | | | | |
|---|---|---|---|---|
| 5,114,776 | A * | 5/1992 | Cesaroni | 428/131 |
| 5,268,213 | A * | 12/1993 | Murakami et al. | 428/163 |
| 5,352,217 | A * | 10/1994 | Curro | 604/378 |
| 5,368,909 | A * | 11/1994 | Langdon et al. | 428/137 |
| 5,397,316 | A * | 3/1995 | LaVon et al. | 604/369 |
| 5,437,653 | A * | 8/1995 | Gilman et al. | 604/378 |
| 5,470,326 | A * | 11/1995 | Dabi et al. | 604/383 |
| 5,536,555 | A * | 7/1996 | Zelazoski et al. | 428/138 |
| 5,578,024 | A * | 11/1996 | Mizutani et al. | 604/380 |
| 5,613,960 | A * | 3/1997 | Mizutani | 604/365 |
| 5,665,083 | A * | 9/1997 | Igaue et al. | 604/370 |
| 5,746,729 | A * | 5/1998 | Wada et al. | 604/378 |
| 5,804,021 | A * | 9/1998 | Abuto et al. | 156/252 |
| 5,817,394 | A * | 10/1998 | Alikhan et al. | 428/137 |
| 5,846,231 | A * | 12/1998 | Fujioka et al. | 604/380 |
| 5,873,868 | A * | 2/1999 | Nakahata | 604/383 |
| 5,976,665 | A * | 11/1999 | Hansson | 428/136 |
| 5,998,696 | A * | 12/1999 | Schone | 604/378 |
| 6,015,936 | A * | 1/2000 | Takai et al. | 604/383 |
| 6,133,501 | A * | 10/2000 | Hallock et al. | 604/369 |
| 6,222,092 | B1 * | 4/2001 | Hansen et al. | 604/378 |
| 6,262,331 | B1 * | 7/2001 | Nakahata et al. | 604/383 |
| 6,280,428 | B1 * | 8/2001 | Lash et al. | 604/385.04 |
| 6,346,097 | B1 * | 2/2002 | Blaney | 604/327 |
| 6,423,045 | B1 * | 7/2002 | Wise et al. | 604/385.12 |
| 6,488,670 | B1 * | 12/2002 | Schild et al. | 604/385.24 |
| 6,648,626 | B1 * | 11/2003 | Eltvedt | 425/436 R |
| 7,005,558 | B1 * | 2/2006 | Johansson et al. | 604/383 |
| 7,067,711 | B2 * | 6/2006 | Kuroda et al. | 604/380 |
| 2003/0004482 | A1 | 1/2003 | Drevik et al. | |
| 2003/0068952 | A1 * | 4/2003 | Hisanaka et al. | 442/394 |
| 2003/0120238 | A1 * | 6/2003 | Gustavsson et al. | 604/383 |
| 2004/0049166 | A1 * | 3/2004 | Chen et al. | 604/380 |
| 2004/0209067 | A1 * | 10/2004 | Muth et al. | 428/314.4 |
| 2004/0265534 | A1 * | 12/2004 | Curro et al. | 428/92 |

FOREIGN PATENT DOCUMENTS

| | | |
|---|---|---|
| EP | 0 304 957 B1 | 3/1989 |
| EP | 0 304 957 B2 | 3/1989 |
| EP | 1 138 301 A3 | 10/2001 |
| JP | 2003-204993 A | 7/2003 |
| JP | 2003-528654 A | 9/2003 |
| WO | WO 01/26595 A1 | 4/2001 |

OTHER PUBLICATIONS

English translation of a Notice of Reasons for Rejection issued Feb. 2, 2010, in corresponding JP Application No. 2006-546888.

* cited by examiner

ABSORBENT ARTICLE WITH THROUGH-SLITS SURROUNDED BY BINDING AREAS

CROSS-REFERENCE TO RELATED APPLICATIONS

The present application claims the benefit of U.S. Provisional Application No. 60/532,575 filed in the United States on Dec. 29, 2003, the entire contents of which are hereby incorporated herein by reference.

TECHNICAL FIELD

The present invention relates to an absorbent article such as a diaper, pant diaper, an incontinence shield, a sanitary towel or the like, comprising an upper, preferably liquid-permeable cover sheet, a lower, preferably liquid-impermeable cover sheet, and an absorption body arranged between the cover sheets, said article defining a longitudinal direction, a front portion in the longitudinal direction, and a rear portion in the longitudinal direction.

The present invention also relates to a method for manufacturing an absorbent article such as a diaper, an incontinence shield, a sanitary towel or the like, comprising an upper, liquid-permeable cover sheet, a lower, preferably liquid-impermeable cover sheet, and an absorption body arranged between the cover sheets, said article defining a longitudinal direction, a front portion in the longitudinal direction, and a rear portion in the longitudinal direction.

BACKGROUND ART

In connection with absorbent articles such as diapers, pant diapers, incontinence shields for adults, and sanitary towels, there has long been a general need for materials and structures which are able to take up, distribute and absorb bodily excretions in a rapid and effective manner. Today's absorbent articles generally have good absorbency with a low risk of leakage and a high degree of comfort for the person wearing the absorbent article.

The requirement for effective absorbency in an absorbent article is important not least in the case of diapers for infants where there is a need for rapid uptake, distribution and absorption of urine and excrement. In this connection, it should be noted that newborn babies and also slightly older infants often produce excrement which is loose and runny in consistency. In today's diapers for infants, there is, for example, a risk of this loose excrement leaking out along the back of the person wearing the diaper. Such leakage may entail a risk of, for example, soiled clothes and bed linen. In general, it may be stated that, in connection with diapers for infants, ever greater demands are being placed on the ability to take up excrement via the surface material and absorption material of a diaper.

According to the prior art, a diaper can be designed with so-called extra inner barriers (inner leg gatherers) which form a seal by means of which excrement can be prevented from running out along the sides of the diaper. Another previously known way of achieving this is to use extra transverse pockets in the diaper, these pockets being designed to prevent leakage at the front or rear edge of the diaper.

With the two abovementioned solutions, leakage of excrement from a diaper is prevented in an effective manner. However, the problem still remains that the excrement can stay on the cover sheet of the diaper and soil the user. In addition, there is a risk of the user experiencing skin irritation in such a situation. This problem has in turn been solved in a known way by using a diaper with an extra cover sheet which comprises relatively large openings, for example a type of opening for taking up urine and excrement.

These solutions provide better protection for certain areas of the skin since the extra cover sheet isolates them. However, the problem still remains here that the excrement cannot penetrate down into the diaper. According to the prior art, this problem has been solved by using special cover sheets with small openings which also allow excrement to penetrate down into the structure.

The problem of the abovementioned solutions is that the absorption material which is located under the cover sheet that has been provided with openings can emerge through the openings and attach to the user's skin. This can involve cellulose fibers, superabsorbent particles or loose fibers of polymer material. This is unsatisfactory because it gives a visual impression of a diaper of poor quality. In addition, it makes cleaning the user's skin difficult, and in the worst cases the user may experience skin irritation.

The reason why the previously known cover sheets with openings do not function satisfactorily is that the openings extend in the x-y plane of the diaper (i.e. an imagined plane extending parallel to the surface of the diaper). The underlying absorption material is exposed in this way.

To get around this problem, it is already known to produce a diaper with openings which extend in the z plane of the diaper (i.e. at right angles to the x-y plane). An example of such a solution is described in Swedish patent number SE 449298.

A disadvantage of the solution according to SE 449298, however, is that the openings in the z direction can be easily compressed when the cover sheet is exposed to pressure during use.

OBJECTS AND SUMMARY

There is therefore a need to solve the problem concerning further improved uptake, distribution and absorption of, in particular, loose excrement in the type of diapers which are used on infants and which are based on openings being formed in the cover sheet of a diaper.

An object of the present invention is to make available an improved absorbent article in which the abovementioned problems are solved and the requirements and needs are satisfied.

The above objects are achieved with an absorbent article of the type mentioned in the introduction, wherein the upper cover sheet, together with an underlying wadding material, defines a laminate which, at least in said rear portion, is designed with at least one through-slit which defines a corresponding opening for passage of bodily excretions through said slit, and said slit is surrounded by binding areas which, together with a resilient action of the wadding material, define a raised area on the surface of said article.

The above objects are also achieved by a method for manufacturing an absorbent article of the type mentioned in the introduction, which method comprises joining together a laminate which comprises said upper cover sheet in conjunction with an underlying wadding material, forming at least one slit in said laminate over a predetermined surface along said article, by which means a corresponding opening is defined for passage of bodily excretions through said slit, and forming binding areas which surround said slit and which, together with a resilient action of the wadding material, define raised areas on the surface of said article.

The invention affords certain advantages. In particular, it may be noted that the invention permits a high speed of admission of excreted bodily fluid and excrement, which significantly reduces the risk of the liquid or excrement streaming out across the surface of the sheet instead of penetrating through the surface. According to a first embodiment of the invention, in which the abovementioned slits are oriented such that a number of hump-shaped areas are formed, excrement can be transferred in through a top sheet and onwards to a wadding material through the open slits, after which it is spread and is finally bound in the underlying wadding material. In this way, the slits and the hump-shaped areas act to prevent excrement leaking out at the user's back. In addition, excrement accumulates in the valleys between said hump-shaped areas. Since the user's skin lies against the top of the humps, which are substantially free from excrement, there is less skin irritation and a higher degree of user comfort.

According to a second embodiment of the invention, in which the abovementioned slits define substantially straight lines extending substantially transversely across the top face of the article, between the latter's side edges, raised areas are obtained which are defined across the top face of the article. In this way, a structure is obtained which effectively slows down and prevents excrement from leaking out at the user's back.

DESCRIPTION OF THE FIGURES

Embodiments of the invention will be described below with reference to preferred embodiments and to the attached drawings, in which.

DETAILED DESCRIPTION OF THE PREFERRED EMBODIMENTS

The present invention will now be described with reference to a number of preferred embodiments which indicate different types of absorbent articles in accordance with the invention. According to a first embodiment, which can be seen from FIG. 1, the absorbent article is a diaper 1 of the disposable type for infants. The diaper 1 comprises a first cover sheet constituting a liquid-permeable top sheet 2. This top sheet 2 is arranged on that side of the diaper 1 which, during use, is intended to be directed towards the person wearing the diaper. The diaper 1 further comprises a second cover sheet constituting a bottom sheet 3 which, during use, is intended to be directed away from the user. The bottom sheet 3 is expediently liquid-tight. A layer of a wadding material 4 is arranged under the top sheet 2. In accordance with what is described in detail below, the top sheet 2 and the underlying wadding material 4 form a liquid-permeable and liquid-transporting laminate which, according to an embodiment of the invention, is used to take up loose and runny excrement in particular. Under the wadding material 4 there is an absorption body, which is not indicated by any reference number in FIG. 1 but will be described below with reference in particular to FIG. 2.

Thus, a structure is formed in the diaper according to an embodiment of the invention which, from the top downwards, comprises a cover sheet 2 and a wadding material 4 (which together constitute a laminate), an absorption body, and a bottom sheet 3.

Figure 1:
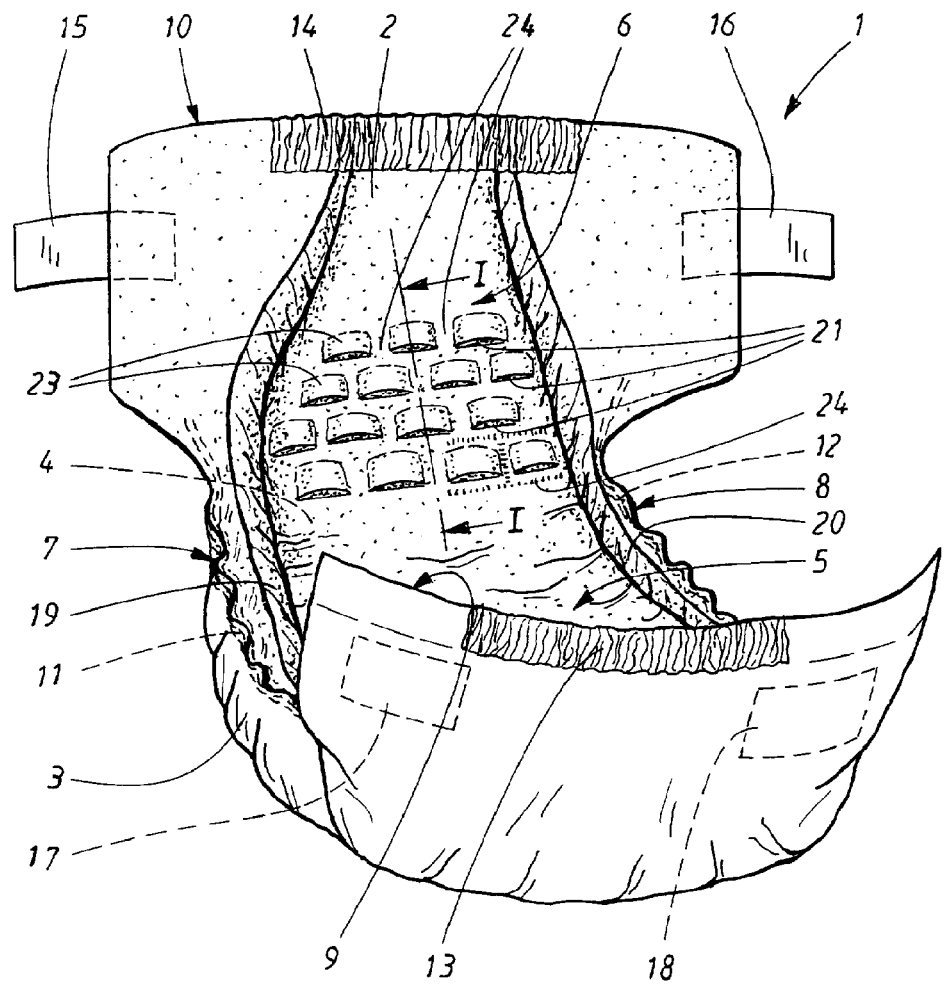
FIG. 1 shows a perspective view of an absorbent article in the form of a diaper for infants, in which diaper an embodiment of the present invention can be used.

The liquid-permeable top sheet 2 according to FIG. 1 expediently consists of a fibrous material, for example a soft nonwoven material, but it can alternatively consist of other materials or material laminates. For example, it can consist of a perforated plastic film, for example of a thermoplastic material such as polyethylene or polypropylene, or a net-like layer of synthetic or textile material. Likewise, different types of laminates of suitable materials can be used as the liquid-permeable top sheet. The nonwoven materials used are preferably synthetic fibers such as polyethylene, polypropylene, polyester, nylon or the like. In addition, mixtures of different fiber types can be used for said nonwoven materials. The top sheet 2 expediently has a pore size which is large enough to let urine pass through even though the fibers in this sheet are hydrophobic.

Thus, the top sheet 2 is preferably a nonwoven material, but, irrespective of the material chosen, the top sheet 2 is intended in a manner known per se to receive and let through liquid excretions from the user and transfer these downwards to the underlying wadding material 4. The wadding material 4 is preferably a suitable hydrophilic material of specific resilience and thickness. Moreover, the underlying bottom sheet 3 is expediently liquid-impermeable and is intended to prevent any leakage of liquid through the wadding material 4 and the absorption body. For this purpose, the bottom sheet 3 can be made of a liquid-impermeable material expediently in the form of a thin and liquid-tight plastic film. For example, plastic films made of polyethylene, polypropylene or polyester can be used. Alternatively, a laminate of nonwoven and plastic film or other suitable material layers can be used as the liquid-tight bottom sheet 3.

As can be seen from FIG. 1, the diaper 1 has a substantially elongate shape and is generally formed to fit around the lower trunk of an infant when in use. The diaper 1 can thus be said to be designed so that it defines a longitudinal direction and a transverse direction. The diaper 1 is designed with a front portion 5 in its longitudinal direction, and a rear portion 6 in its longitudinal direction. When the diaper 1 is in use, the front portion 5 is positioned so that it is directed towards the user's belly and down towards the groin area, while the rear portion 6 is positioned so that it is directed towards the user's buttocks. The boundary between the front portion 5 and rear portion 6 does not need to be defined with exact dimensions and does not occur at a specified transverse position for example, but instead along an extended transition area at the user's crotch region. As regards the function of the diaper 1, the rear portion 6 is basically designed to take up a greater amount of excrement from the user than is the front portion 5. The rear portion 6 can therefore be said to have a position and extent corresponding to the area where excrement may be expected to accumulate.

The diaper 1 is further designed with two elongate side edges 7, 8 and two transverse end edges 9, 10, more specifically a front end edge 9 and a rear end edge 10. The two side edges 7, 8 are designed with elastic arrangements 11, 12 (which are shown by broken lines in FIG. 1), for example in the form of longitudinal elastic threads, bands or the like. In this way, elastic sections are defined, so-called leg elastics, at the side edges 7, 8, so that each side edge 7, 8 bears on and provides a seal against the inner surface of the user's leg in order to prevent leakage of urine and excrement.

Moreover, the diaper 1 comprises further elastic elements 13, 14, preferably in the form of two elasticated portions along the front end edge 9 and the rear end edge 10, respectively. These elastic elements 13, 14 are designed to close against the user's belly and back, respectively, as a result of which the diaper 1 is given the required fit and comfort during use.

To fit the diaper 1 on the user, it is additionally designed with two tape-like fastening strips 15, 16 which are arranged along respective side edges 7, 8 near the rear edge 10. The fastening strips 15, 16 are intended to cooperate and are secured in a releasable manner against corresponding fastening areas 17, 18 (which are indicated by broken lines in FIG. 1) at the front end edge 9. The fastening strips 15, 16 can be secured on the fastening areas 17, 18 by means of the fastening strips 15, 16 being provided with a suitable adhesive for example, or alternatively by their being designed as velcro-type fasteners or in some other suitable manner.

The diaper is further designed with two longitudinal side barriers 19, 20 which run inside of each side edge 7, 8 and are designed as longitudinal edges extending up from the surface of the diaper 1, i.e. so that they prevent leakage of excrement and urine sideways out of the diaper 1. The side barriers 19, 20 are expediently provided with elastic elements (not shown in FIG. 1) which are intended to raise the respective side barrier 19, 20 in a direction substantially at right angles from the plane of the top sheet 2. In this way, effective barriers are formed which prevent said leakage.

The diaper 1 according to the invention is especially suitable for newborn babies. In such an application, the length of the diaper 1 is less than 400 mm, while its width is less than 300 mm. However, the invention is not limited to any specific sizes as regards the external dimensions of the diaper, and instead it can be adapted to different users of different sizes.

Figure 2:
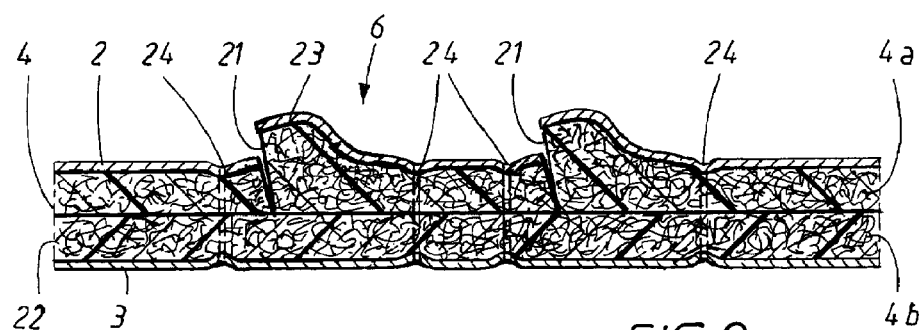
FIG. 2 is a cross-sectional view of the diaper according to FIG. 1, along the line I-I.

A basic principle behind the present invention will now be described in detail with reference to FIG. 1 and FIG. 2, where FIG. 2 is a cross-sectional view along the line I-I in FIG. 1. As is shown in the figures, the laminate comprising the liquid-permeable top sheet 2 and the wadding material 4 is cut through at certain positions by a number of slits 21. Through these openings, the wadding material 4 is exposed for passage and accumulation of bodily excretions from the user. It should be noted that the openings which are defined by the slits 21 extend in the z direction of the diaper 1 (see in particular FIG. 2), i.e. extend in a direction which is substantially at right angles to the plane along which the top sheet 2 is oriented. According to the embodiment shown, the slits 21 are placed in a uniform pattern, as can be seen from FIG. 1, by which means the slits 21 and the formation of the top sheet 2 form a grid-like structure, which is preferably positioned at the rear portion 6 of the diaper 1. In this way, the openings which are defined by the slits 21 are positioned within that area of the diaper 1 where excrement from the user can be expected to accumulate during use of the diaper 1. According to the embodiment shown, the slits 21 are placed in a number of rows which all run along the transverse direction of the diaper 1. As will be described below with reference to FIGS. 3-7, a number of different configurations can be chosen for the position and design of these slits 21 within the scope of the invention.

As has been mentioned above, and as will be seen in particular from FIG. 2, an absorption body 22 is arranged between the laminate and the bottom sheet 3, i.e. on top of the bottom sheet 3 but under the wadding material 4. In the embodiment according to FIG. 2, the laminate, as has been mentioned above, comprises a top sheet 2 and a wadding material 4. According to an alternative embodiment, which is not shown in any of the figures, the laminate can further comprise a fibrous sheet under the wadding material. This further sheet is then also expediently a nonwoven (like the top sheet 2) and will be placed on top of the absorption body 22.

The main purpose of the position and design of the slits 21 is to allow excrement, which in the case of infants can be expected to be loose and runny in consistency, to pass quickly and efficiently through each slit 21 and down to the underlying wadding material 4. In this way, excrement can be taken up and bound to the wadding material 4. A further effect of the slits 21 is that they have a decelerating effect which to a great extent prevents excrement from leaking out at the user's back, i.e. past the rear end edge 10. By virtue of the top sheet 2 being provided with slits, the underlying wadding material 4 is exposed in the z direction in each opening formed. This opening at each hump thus slows down the spread of excrement and additionally defines a storage space for excrement, so that contact of the excrement with the user's skin is reduced.

By means of the position and design of the slits 21, and by virtue of the inherent resilience and thickness of the wadding material 4, mounds are formed, i.e. hump-shaped areas 23, in the top sheet 2, i.e. uniformly placed elevations of the material on the top face of the diaper 1. The height and elasticity of each hump-shaped area 23 is determined, inter alia, by the properties of the underlying wadding material 4.

By virtue of the slits 21 being positioned in the rear portion 6 of the diaper 1, the humps 23 are also positioned substantially under the user's buttocks. By virtue of the fact that the humps 23 have a certain extent in a direction out from the surface of the diaper 1, in the z direction, excrement is accumulated in the "valleys" which are defined between the humps 22. In addition, the wadding material 4 is less compressed in that part of the hump which adjoins the slit 21, for which reason excrement can be easily taken up by the wadding material. This means in turn that the user will feel the top sheet 2 of the diaper as very dry, which is of course an advantage as regards user comfort. In addition, this reduces the risk of the user experiencing skin irritation.

In the manufacture of the diaper, the abovementioned laminate is first obtained by means of the top sheet 2 being bound to the wadding material 4. This binding is preferably of the thermal binding kind, which can be used to create binding areas 24 (see FIG. 2) which are then used to hold the top sheet 2 together with the wadding material 4. Thereafter, slits are formed by, for example, scissors, rotating blades, punching or the like, through substantially the whole laminate, whereupon the laminate is placed on the absorption body 22. In this way, the slits 21 are formed in the top sheet 2, and the underlying wadding material 4 is deformed by the slitting as is shown in FIG. 2. The humps 23 are then formed as a consequence of the resilience or "spring" force of the wadding material 4. During slitting, the uppermost fibers in the wadding material 4 are cut so that this material springs back and rises in the opening which is formed. The positioning of the binding areas 24 in relation to the slits 21 is therefore of importance and is selected so as to obtain good resilience. It is therefore the resilience of the wadding material that gives the humps their height in the z direction.

The actual process of binding the laminate together and obtaining the slits in the laminate is not shown in detail here, but it can expediently be based on the laminate being obtained in the form of a material web which is first fed through a binding station for thermal binding and then through a slitting station where the laminate is cut through at suitable positions with a number of blades. After the binding of the cover sheet 2 to the wadding material 4, and after the laminate thus formed has been slit, the whole laminate is placed on the absorption sheet 22. Thereafter, the bottom sheet 3 can be applied. It is also possible to apply a further material sheet on the underside of the laminate, that is to say between the wadding material 4 and the absorption sheet 22. In this way, the openings in the laminate are prevented from spreading out in an undesired way in the x-y plane, which can happen in the event of inadvertent stretching of the material sheets, for example when applying the laminate on the absorption sheet 22.

Figure 3:
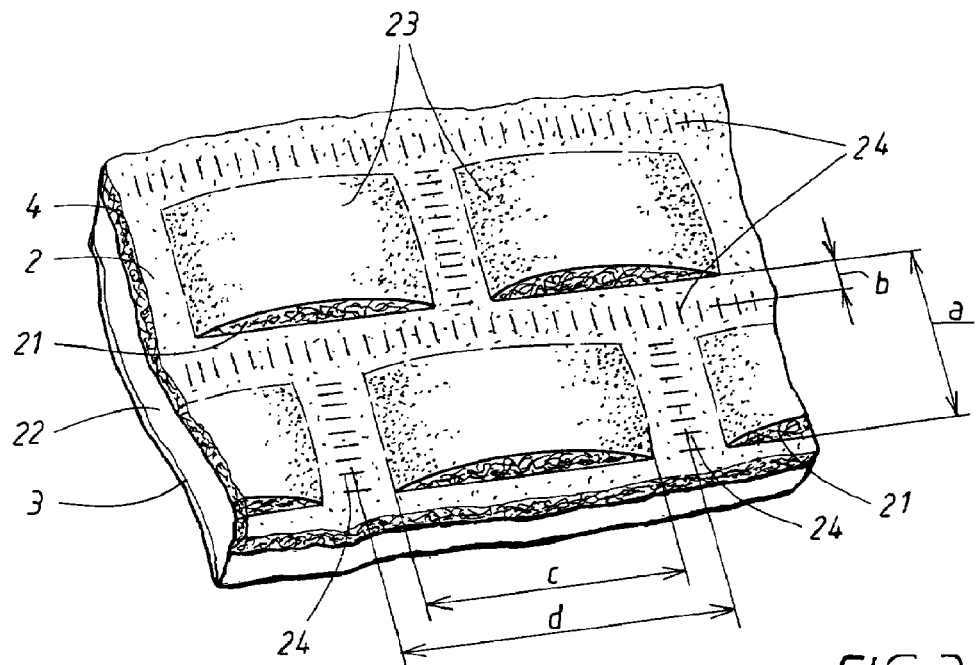
FIG. 3 is a slightly enlarged perspective view of the diaper according to FIGS. 1 and 2, showing the main features of the embodiment of the invention in detail.

The structure and function of an embodiment of the invention will now be explained in more detail with reference to FIG. 2 and also FIG. 3, which is a slightly enlarged perspective view of a section of the rear portion 6 of the diaper 1. FIGS. 2 and 3 show how the top sheet 2 is cut along certain areas so that it defines a number of slits 21, which provide an open passage extending in the z direction through the upper surface of the top sheet 2 and down to the underlying wadding material 4. The wadding material 4 preferably comprises a soft and relatively thick material, which functions as a transporting and distributing layer for liquid excrement and urine passing through the top sheet 2 (i.e. either through the slits 21 or through the top sheet 2 itself). The wadding material preferably comprises a continuous layer lying along the entire surface of the diaper 1. Alternatively, the wadding material can be placed at only part of, or parts of, the surface of the diaper. The absorption body 22 comprises a highly absorbent material, for optimal absorption and storage of bodily excretions.

According to the embodiment, the diaper 1 is designed so that the wadding material in the rear portion 6 of the diaper 1 is preferably thicker than the wadding material in the front portion (see FIG. 1) of the diaper 1. More precisely, the wadding material has a much greater bulk (i.e. volume per unit of weight) in the rear portion 6 of the diaper 1 where most excrement is expected to accumulate and where the slits 21 in the top sheet 2 are also cut out. In this way, the wadding material layer 4 is used optimally to take up excrement, which of course can be expected to take place mainly in the rear portion 6.

For the wadding material layer 4 to be able to take up large amounts of liquid quickly, it has a fiber structure with relatively large pores, i.e. with a capillary structure which permits effective uptake of liquid. The wadding material layer 4 is preferably of the fiber wadding type which can be bound or unbound and which can be based on synthetic or natural fibers. Through suitable choice of wadding material, a desired structure of the humps 23 is also obtained. More specifically, the choice of fibers in the wadding material layer 4, and the latter's density and elasticity or resilience, determines the tendency of the wadding material 4 to press upwards in the areas around the slits 21, so that the abovementioned upwardly projecting humps 23 can be formed. Elasticity or resilience is to be understood as meaning that the material has an ability to assume, or seek to assume, its original thickness or height after compression. To obtain humps 23 which are high in relation to the level of the rest of the top sheet 2, and thus also obtain distinct and large openings defined by the slits 21, material with particularly high resilience can be used in the wadding material 4 at the rear portion 6 of the diaper 1. This will be described in detail below.

The wadding material layer 4 is primarily intended as a transport layer for rapid transport of bodily fluids down to the absorption body 22. In other words, the wadding material layer 4 does not have to be highly absorbent. The underlying high-absorbency layer 22 is, by contrast, intended for a high degree of absorption of liquid and, for this purpose, is expediently made of cellulose fluff pulp. The highly absorbent material in the absorption body 22 can also include so-called superabsorbents, which are polymer compounds with the ability to absorb several times their own weight of liquids, such as bodily fluids. The absorption body 22 can alternatively consist of absorbent synthetic fibers, or mixtures of natural fibers and synthetic fibers.

The absorption body 22 can be designed as is shown in FIG. 2, or it can alternatively be designed in a way in which superabsorbents are admixed. The absorption body can include different sheets of material or a single sheet with good properties as regards the uptake, spread and storage of bodily fluids.

As is shown in FIGS. 2 and 3, the diaper 1 is preferably joined together by means of ultrasound welding so that binding areas 24 are defined. These binding areas 24 comprise a number of lines which bind the top sheet 2 to the wadding material 4 and are placed in a predefined manner close to the slits 22. These binding areas 24 are indicated also in FIG. 1. As can also be seen in FIG. 2 and FIG. 3, these binding areas 24 are positioned so that they hold the material layers 2, 4 together about the humps 23 formed on the top face of the diaper 1. As can be seen in particular from FIG. 3, these binding areas 24 additionally define a kind of grid system with straight lines in the longitudinal direction and transverse direction of the diaper 1. These lines surround the various humps 23.

As has been stated above, the diaper 1 is joined together preferably by thermal binding. However, the invention is not limited to this method, and instead the joining can also be done by means of adhesive binding or some other suitable method of forming the above-described binding areas 24. Regardless of which joining method is chosen, each binding area 24 can be designed as a series of discrete points, continuous lines, wide fields or other similar configurations. Various parameters such as the width of the binding areas (in the case where these are wide fields) or the position and dimensions of the points (in the case of a series of points) can also be varied within the scope of the invention. To obtain a strong bond between the material sheets, it is possible to choose the fiber materials in the cover sheet 2 and the wadding material 4 in such a way that fibers from both sheets are melted together at the binding areas 24.

As regards the width of each binding area 24, it can be stated that this is expediently of the order of 0.5-15 mm in a suitable design of a diaper. The binding areas 24 are also positioned in a predetermined manner so that the slits 21 (and thus also the humps 23) will be able to be formed. As can be seen from FIG. 3, two specific dimensions, a and b, can be defined in the longitudinal direction of the diaper. It is assumed here that the binding areas 24 are designed as a grid system with substantially straight lines extending in the longitudinal direction and transverse direction of the diaper. It is additionally assumed that the slits 21 are placed in line with one another in the transverse direction of the diaper 1. The first-mentioned dimension a relates to the distance between two neighbouring slits 21, as seen in the longitudinal direction of the diaper. The last-mentioned dimension b relates to the distance between a slit 21 and the binding area 24 positioned in front of the slit 21. According to the embodiment shown in FIGS. 1-3, the distance a is of the order of 10-100 mm, preferably 15-50 mm, while the distance b is of the order of up to 10 mm, preferably 1-10 mM.

As is shown in FIG. 3, each slit 21 additionally defines a length c, that is to say in the transverse direction of the diaper, which is preferably of the order of 10-20 mm. This means that the binding areas 24 which run in substantially the longitudinal direction of the diaper between two neighbouring humps 23 are arranged at a distance d which slightly exceeds the length c of each slit 21.

The details of the various preferred dimensions a, b, c, d given here can also be applied to the embodiments which will be described below with reference to FIGS. 4-7.

Figure 4:
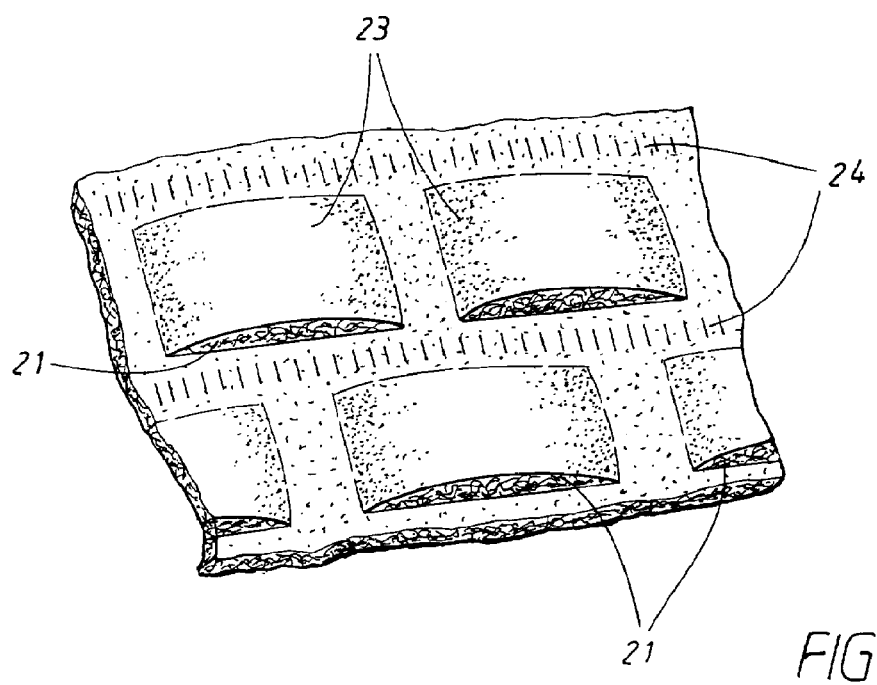
FIG. 4 is a perspective view of a second embodiment of the invention.

According to a further embodiment of the invention, which is shown in FIG. 4, there are no binding areas running in the longitudinal direction of the diaper 1, and instead the only binding areas 24 which are used run in the transverse direction of the diaper. The positioning and length of the slits 21 provide the conditions for forming humps of the type which have been described above.

Figure 5:
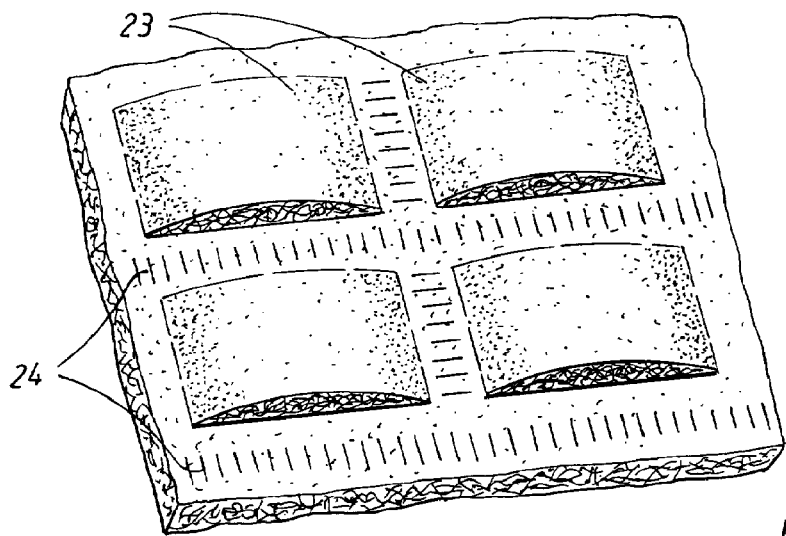
FIG. 5 is a perspective view of a third embodiment of the invention.

According to a third embodiment of the invention, which is shown in FIG. 5, not every second row of humps 23 is offset in the transverse direction of the diaper, as is the case in the embodiments according to FIGS. 3 and 4, and instead the humps 23 are placed as regular grids across the surface of the diaper 1. In other words, the humps 23 lie in line with one another both in the transverse direction and in the longitudinal direction of the diaper. This third embodiment is provided with binding areas 24 in the longitudinal direction and the transverse direction of the diaper, or, alternatively, only in the transverse direction of the diaper (see FIG. 3).

Figure 6:
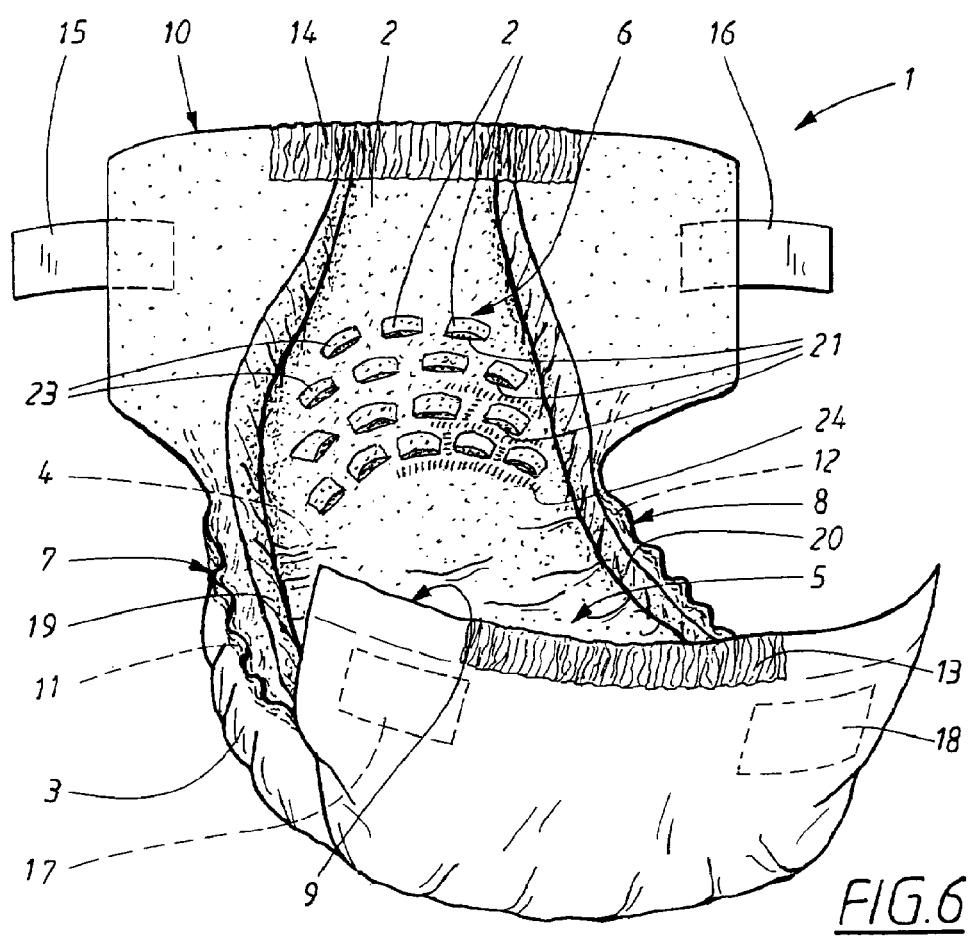
FIG. 6 is a perspective view of an absorbent article in the form of a diaper which is designed according to a fourth embodiment of the invention.

According to a fourth embodiment of the invention, which is shown in a perspective view in FIG. 6, the humps 23 can be placed in an arrangement which, in contrast to FIGS. 3-5, is not oriented along straight lines. Instead, the humps 23 here are placed along an arc-like or fan-like structure in order in this way to adapt the ability of the diaper 1 to accumulate excrement to the body shape of the person using the diaper 1. In this embodiment, the openings which are defined by the slits 21 are thus directed more distinctly inwards towards the crotch region of the user.

Figure 7:
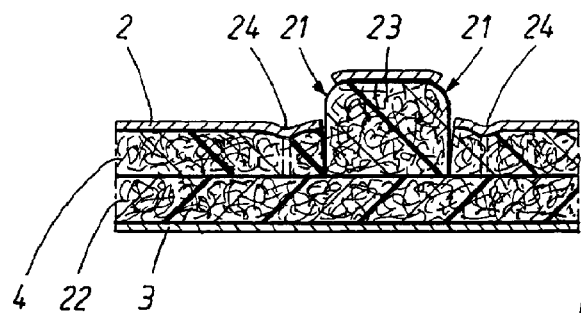
FIG. 7 is a cross-sectional view of the invention which in principle corresponds to the cross section according to FIG. 2, but showing a further embodiment of the invention.

FIG. 7 is a cross-sectional view which essentially corresponds to FIG. 2, but which shows a further embodiment of the invention in which two slits 21 are made at each hump 23. Here, therefore, the material is slit at both the front edge and the rear edge of each hump 23, instead of only at the front edge, which is the case with the abovementioned embodiments (see FIG. 2 for example). In this embodiment, the top sheet 2 defines a kind of arc-like shape on each hump 23. The alternative embodiments which are shown in FIGS. 4-6 can also be designed with double slits as shown in FIG. 7.

In the embodiment which is shown in FIG. 7, the distance between two slits 21 (i.e. across the hump 23) can be of the order of 4-100 mm, preferably 10-40 mm. The distance between two slits, viewed across the binding area 24, can moreover be of the order of 3-20 mm, preferably 5-15 mm.

It will be noted that although the binding areas 24 can consist of the straight lines shown in FIGS. 3-5, other configurations of weld seams can alternatively be chosen, for example short "broken" lines or points, which are then positioned in such a way as to permit suitable formation of the humps 23. It will likewise be noted that the weld seams do not have to be in the form of straight lines, and instead curved weld seams may be expedient in some applications (see FIG. 6). The overall requirement satisfied by the invention is that of ensuring that the slits 21 define openings which extend in the z direction of the diaper 1 and permit optimal passage, to the wadding material 4, of the excrement collecting in the rear portion 6 of the diaper 1. It should be noted here that the openings defined at the slits 21 are so configured that an especially effective uptake of excrement is obtained in a direction along the diaper 1 running rearwards and substantially parallel to the top sheet 2 (see in particular FIG. 2). In this way, excrement is transferred substantially straight in to the openings at the slits 21.

According to the embodiment shown, the humps 23 are placed in the form of substantially rectangular grids which are ordered in a number of substantially parallel rows along the longitudinal direction of the diaper. These rows extend transversely across the diaper 1, i.e. between the two side barriers 19, 20 of the diaper (see FIG. 1). Every second row of humps 23 is preferably slightly offset, in the transverse direction of the diaper, in relation to the neighbouring row(s). In this way, the humps 23 are positioned so that they form a staggered and "overlapping" pattern so that a hump 23 in a given row lies in line with a gap between two humps 23 of a neighbouring row. This means in turn that the slits 21 can provide maximum access to loose excrement which is then allowed to pass to the underlying wadding material 4.

The position and dimensions of the slits 21 and humps 23 can vary within the scope of the invention. As an alternative to the relatively uniform patterns shown in FIGS. 1-7, the humps 23 can form any desired configurations which provide the desired uptake of excrement in particular. Likewise, the dimensions of the slits 21 and humps 23 can vary within the scope of the invention. Nor, for example, do the humps have to be rectangular or square, and instead they can be another shape, for example semicircular. Moreover, the humps do not all have to be the same size and shape, and instead different types of humps can be present in different areas of the rear portion 6 of the diaper.

The height of the humps 23 above the surface of the top sheet 2 can also vary within the scope of the invention. A greater height generally gives better access to the underlying wadding material 4, which, as is shown for example in FIG. 3, can be discerned in the openings which are defined by the slits 21. A greater height of the humps 23 also gives the user an improved feeling of dryness, because excrement is then accumulated to a greater extent in the valleys between the humps 23, which in turn slows down the spread of the excrement and additionally isolates the user's skin from contact with the excrement.

An additionally improved effect can be achieved if the top sheet 2 is slit in at least part of the transverse gable ends of each hump 23, i.e. so that a greater part of the "grid" surrounding each hump 23 is opened for exposure of the underlying wadding material 4. The wadding material 4 will then also lift the top sheet 2 to a greater extent, so that the humps 23 are effectively raised. In addition, gables are thus formed where it is open directly into the wadding material 4.

According to an alternative embodiment, humps can be formed by punching squares from a complete sheet of wadding material. The remaining wadding material then defines humps. These are covered by cover material which, for example, is welded or glued firmly in the valleys between the humps and is slit where the wadding squares lie.

The inherent elasticity and hardness of the wadding material 4, and thus also its resilient properties, create conditions for forming the abovementioned humps 23. A further factor determining the form of the humps 23 is the thickness of the wadding material 4, and also the positioning and dimensioning of the slits and the binding areas.

Practical trials have shown that a permanent compression of less than 20% and a basis weight of 60-200 g/m2 can be suitable material parameters for the wadding material. A measure of the permanent compression is obtained by first measuring the difference between the thickness of the material after a certain compression force has been applied and thereafter removed (the material having been allowed to recover) and the original thickness of the material. This value is then divided by the original thickness and gives a value of the permanent compression of the material in question. A customary measurement method for permanent compression is ISO 1856:1980.

Figure 8:
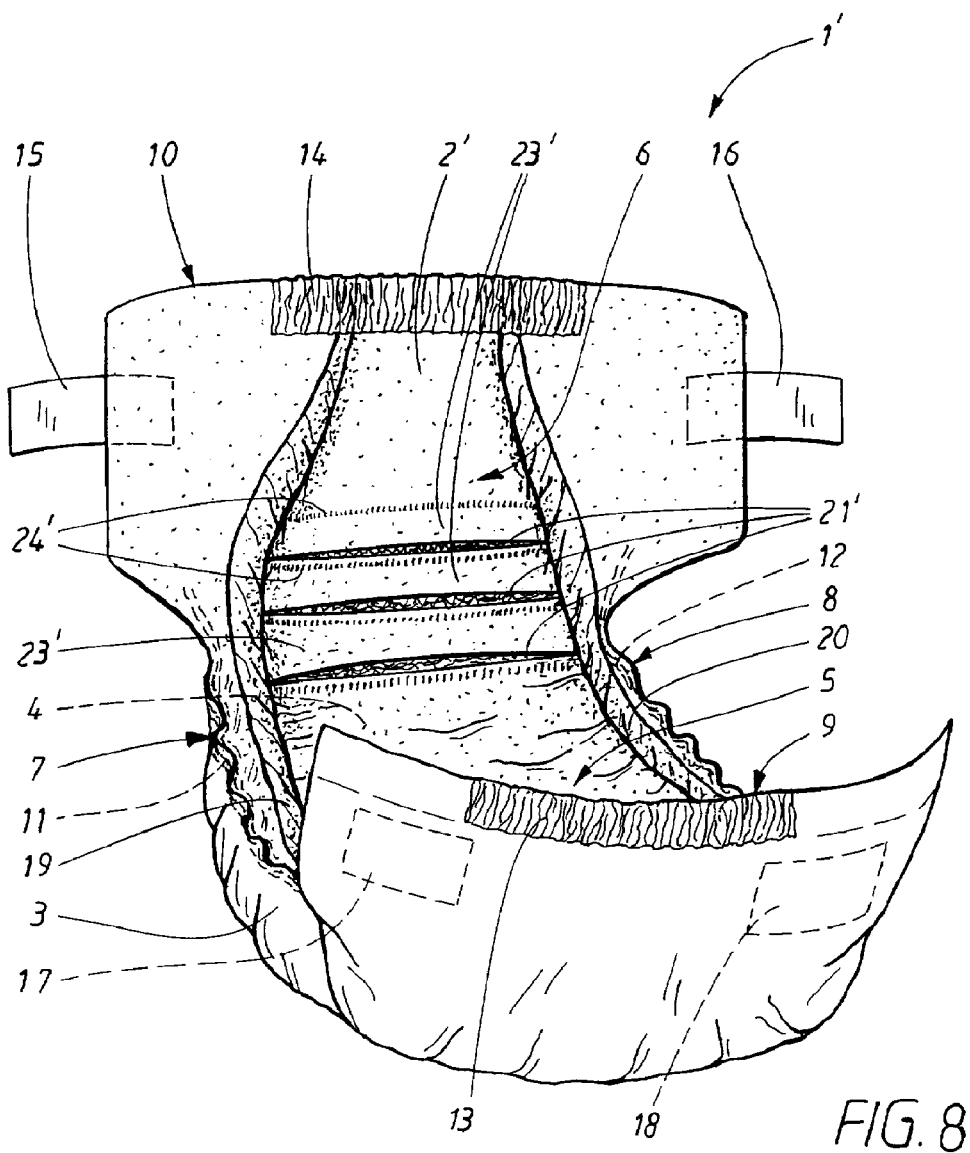
FIG. 8 shows a perspective view in which the article has been formed in accordance with a further alternative embodiment.

An alternative embodiment of the invention will now be described with reference to FIG. 8 which shows a diaper 1' of substantially the same type as is shown in FIG. 1, but where the top sheet 2' of the diaper is designed in an alternative way. The components in FIG. 8 which correspond to like components in FIG. 1 have been indicated by the same reference numbers as in FIG. 1. In contrast to the embodiments shown in FIGS. 1-7, FIG. 8 describes a variant of the invention in which relatively long slits 21' have been formed and run transversely with respect to the longitudinal direction of the diaper 1'. More precisely, in this embodiment a number of these transverse slits 21' have been used which preferably run between respective side barriers 19, 20 of the diaper 1'. In FIG. 8, three such slits 21' are shown, but the number of slits 21' can vary within the scope of the invention.

In the embodiment according to FIG. 8, the different material layers of the diaper 1' are also joined together at suitable positions. Ultrasound welding is expediently used to form a number of binding areas 24, expediently in the form of a long line running in front of each slit 21'. In this way, a joined structure is formed with large transverse openings in the z direction, which facilitate uptake of excrement in an underlying wadding material 4.

The end portion of each slit 21' can be secured in the respective side barrier 19, 20 of the diaper 1'. In this way, each end portion of the slits 21' will lift together with the side barriers 19, 20 in an effective manner. As in the case of the hump-shaped areas 23 shown in FIGS. 1-3, the height of the transverse raised areas 23' according to FIG. 8 is also affected by the properties of the materials included in the underlying wadding material 4, e.g. its bulk, elasticity and resilience.

FIG. 8 shows how, at the openings which are defined at each slit 21', the material in the underlying wadding material 4 is exposed. As in the embodiments according to FIGS. 1-7, the main principle of the function of the diaper 1' according to FIG. 8 is that the top sheet 2' is provided with slits 21' of such a type that the wadding material 4 is exposed for passage of bodily excretions through said slits 21'. The embodiment according to FIG. 4 is especially effective as regards the ability to slow down excrement so that the latter does not leak out via the rear end edge 10 of the diaper 1'.

As regards dimensions, the embodiment according to FIG. 8 is designed so that the length of the slits 21' is preferably substantially the same as or slightly smaller than the width of the finished diaper 1' between the side barriers 19, 20. In addition, these long transverse slits can alternatively be curved, i.e. as an alternative to the substantially straight slits 21' shown in FIG. 8.

The invention is not limited to the embodiments described above and instead it can be varied within the scope of the attached claims and equivalents thereof. For example, the principle behind the invention can be applied not just to diapers, but also, for example, to incontinence shields for collecting urine and excrement from adults suffering from incontinence. Likewise, the invention can in principle be used in sanitary towels.

The components involved can have different dimensions. For example, the size, height and position of the humps (according to FIGS. 1-7) and the raised areas (according to FIG. 8) can vary. Likewise, the wadding material 4 can be designed in different ways, for example with different types of material of suitably chosen dimensions and material properties.

The structures which have been described above can also be combined with other suitable constructions for collecting bodily excretions. For example, an absorbent article according to the invention can be supplemented with other types of pockets, barrier structures and surface material in order to further improve the function as regards collection of excrement, for example.

What is claimed is:

1. An absorbent article having a longitudinal direction, a front portion in the longitudinal direction, and a rear portion in the longitudinal direction, said absorbent article comprising:
   a liquid-permeable cover sheet,
   a second cover sheet, and
   an absorption body comprising at least an absorbent material arranged between the cover sheets,
   wherein the liquid-permeable cover sheet and an underlying wadding material form a laminate, said laminate including, at least in said rear portion, at least one through-slit extending from a first end positioned at the liquid-permeable cover sheet substantially through both the liquid-permeable cover sheet and the wadding material to a second end, thereby defining an opening for passage of bodily excretions through said slit,
   wherein said slit is substantially a straight line extending in a transverse direction of the article, and is at least partially surrounded by binding areas which, together with a resilient action of the wadding material, define raised areas above a surface of the liquid-permeable cover sheet at the binding areas, the surface of the liquid-permeable cover sheet facing a skin of a user when said article is in use, and
   wherein the absorbent material is positioned between the second end of the slit and the second cover sheet.

2. The absorbent article according to claim 1, wherein the opening at said slit extends in a direction which is substantially at right angles to a plane along which the surface of the article extends.

3. The absorbent article according to claim 1, wherein the opening at each slit faces substantially in the direction towards said front portion of the article.

4. The absorbent article according to claim 1, wherein said binding areas are formed by thermal binding.

5. The absorbent article according to claim 1, wherein said binding areas form lines, points or elongate areas extending along a number of substantially parallel lines in the transverse direction of said article.

6. The absorbent article according claim 5, wherein the absorbent article comprises a slit between two binding areas.

7. The absorbent article according to claim 5, wherein the absorbent article comprises two slits between two binding areas.

8. The absorbent article according to claim 1, wherein said binding areas form lines, points or elongate areas extending along a number of substantially parallel lines in the longitudinal direction of said article.

9. The absorbent article according to claim 1, wherein said binding areas form lines, points or elongate areas which define an arc-shaped configuration so that the openings which are formed by each slit face towards an imagined position for the crotch region of the person using said article.

10. The absorbent article according to claim 1, wherein the absorbent article comprises a number of slits which are oriented so that a corresponding number of raised areas define humps which are formed along a number of rows running substantially at right angles to said longitudinal direction of the article, neighbouring rows being offset so that a hump in one row is in line with a gap between two humps of a neighbouring row.

11. The absorbent article according to claim 1, wherein the at least one slit is positioned such that said wadding material is exposed for taking up bodily excretions with a direction of spread which is substantially parallel to said upper cover sheet.

12. The absorbent article according to claim 1, wherein said slit is positioned substantially at said rear portion of said article, said rear portion being defined as an area at which excrement may be expected to accumulate.

13. The absorbent article according to claim 1, wherein said wadding material has a substantially greater bulk in said rear portion than in the rest of the article.

14. The absorbent article according to claim 1, wherein the distance between two neighbouring binding areas in the longitudinal direction of the article is approximately 10-100 mm.

15. The absorbent article according to claim 1, wherein the distance between a binding area and a slit behind it in the longitudinal direction of the article is up to approximately 10 mm.

16. The absorbent article according to claim 1, wherein the length of said slit in the transverse direction of the article is approximately 10-20 mm.

17. The absorbent article according to claim 1, wherein the absorbent article is a diaper, an incontinence shield or a sanitary towel.

18. The absorbent article according to claim 1, wherein the distance between two neighbouring binding areas in the longitudinal direction of the article is approximately 15-50 mm.

19. The absorbent article according to claim 1, wherein the distance between a binding area and a slit behind it in the longitudinal direction of the article is up to approximately 1-10 mm.

20. The absorbent article according to claim 1, wherein the second cover sheet is liquid-impermeable.

21. The absorbent article according to claim 1, wherein said binding areas bind the liquid-permeable cover sheet to the wadding material at predetermined locations on said laminate, said laminate also including predetermined locations without binding areas, wherein said at least one through-slit is formed in a predetermined location without a binding area such that the wadding material rises into the opening when cutting the at least one through-slit and forms the raised area.

22. The absorbent article according to claim 1, wherein the raised areas are directly covered by the liquid-permeable cover sheet.

23. The absorbent article according to claim 1, wherein the raised areas are at least partly directly covered by the liquid-permeable cover sheet.

24. An absorbent article having a longitudinal direction, a front portion in the longitudinal direction, and a rear portion in the longitudinal direction, said absorbent article comprising:
  a liquid-permeable cover sheet,
  a second cover sheet, and
  an absorption body comprising at least an absorbent material arranged between the cover sheets,
  wherein the liquid-permeable cover sheet and an underlying wadding material form a laminate, said laminate including, at least in said rear portion, at least one through-slit extending from a first end positioned at the liquid-permeable cover sheet substantially through both the liquid-permeable cover sheet and the wadding material to a second end, thereby defining an opening for passage of bodily excretions through said slit,
  wherein said slit is at least partially surrounded by binding areas which, together with a resilient action of the wadding material, define raised areas above a surface of the liquid-permeable cover sheet at the binding areas, the surface of the liquid-permeable cover sheet facing a skin of a user when said article is in use, wherein adjacent each slit is a first raised area extending from the slit towards the rear portion, and adjacent each slit is a second raised area extending from the slit towards the front portion, the first and second raised areas are immediately across a longitudinal direction of the slit, and the first and second raised areas have different levels in a direction substantially perpendicular to a plane of the liquid-permeable cover sheet, and
  wherein the absorbent material is positioned between the second end of the slit and the second cover sheet.

25. The absorbent article according to claim 24, wherein the first raised areas are higher than the second raised areas.

26. The absorbent article according to claim 24, wherein the first and second raised areas exclude an end of the slit in a traverse direction of the slit.

27. An absorbent article having a longitudinal direction, a front portion in the longitudinal direction, and a rear portion in the longitudinal direction, said absorbent article comprising:
  a liquid-permeable cover sheet,
  a second cover sheet, and
  an absorption body comprising at least an absorbent material arranged between the cover sheets,
  wherein the liquid-permeable cover sheet and an underlying wadding material form a laminate, said laminate including, at least in said rear portion, at least one through-slit extending from a first end positioned at the liquid-permeable cover sheet substantially through both the liquid-permeable cover sheet and the wadding material to a second end, thereby defining an opening for passage of bodily excretions through said slit,
  wherein said slit is substantially a straight line extending in a transverse direction of the article, and is at least partially surrounded by binding areas which, together with a resilient action of the wadding material, define raised areas above a surface of the liquid-permeable cover sheet at the binding areas, the surface of the liquid-permeable cover sheet facing a skin of a user when said article is in use, wherein adjacent each slit is a first raised area extending from the slit towards the rear portion, and adjacent each slit is a second raised area extending from the slit towards the front portion, the first and second raised areas are immediately across a longitudinal direction of the slit, and the first and second raised areas have different levels in a direction substantially perpendicular to a plane of the liquid-permeable cover sheet, and
  wherein the absorbent material is positioned between the second end of the slit and the second cover sheet.

28. The absorbent article according to claim 27, wherein the first raised areas are higher than the second raised areas.

29. The absorbent article according to claim 27, wherein the first and second raised areas exclude an end of the slit in a traverse direction of the slit.

* * * * *